US010682193B2

(12) United States Patent
Choi et al.

(10) Patent No.: US 10,682,193 B2
(45) Date of Patent: Jun. 16, 2020

(54) GUIDING APPARATUS FOR REMOTE MEDICAL TREATMENTS

(71) Applicant: KOREA INSTITUTE OF SCIENCE AND TECHNOLOGY, Seoul (KR)

(72) Inventors: Wooseok Choi, Seoul (KR); Sung Chul Kang, Seoul (KR); Jae-In Hwang, Seoul (KR); Woosub Lee, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 296 days.

(21) Appl. No.: 15/717,938

(22) Filed: Sep. 28, 2017

(65) Prior Publication Data

US 2018/0263719 A1     Sep. 20, 2018

(30) Foreign Application Priority Data

Mar. 20, 2017  (KR) .......................... 10-2017-0034578

(51) Int. Cl.
*A61B 34/00*    (2016.01)
*B25J 9/10*     (2006.01)
(Continued)

(52) U.S. Cl.
CPC ............ *A61B 34/71* (2016.02); *A61B 90/361* (2016.02); *A61B 90/50* (2016.02); *B25J 9/104* (2013.01);
(Continued)

(58) Field of Classification Search
CPC .. A61B 34/71; A61B 2034/715; B25J 9/1045; B25J 9/104; B25J 9/106; B25J 9/1065
See application file for complete search history.

(56) References Cited

U.S. PATENT DOCUMENTS 4,383,455 A  *  5/1983  Tuda .................... B25J 9/104
                                                   16/401
8,979,042 B2 *  3/2015  Doi ..................... F16M 11/2021
                                                   248/123.11
(Continued)

FOREIGN PATENT DOCUMENTS

JP         3618506 B2    2/2005
JP       2010194307 A    9/2010
(Continued)

OTHER PUBLICATIONS

Jong-Tae Seo et al., "Design of a New Counter-Balancing Stackable Mechanism", IEEE International Conference on Robotics & Automation, 2014, pp. 2372-2377, Hong Kong, China.
(Continued)

*Primary Examiner* — Jeremy R Severson
(74) *Attorney, Agent, or Firm* — Cantor Colburn LLP

(57)                ABSTRACT

A guiding apparatus for remote medical treatments includes a first pivoting link pivotally connected to a pivot shaft, a second pivoting link pivotally connected to the first pivoting link, a driver pulley member capable of fixing the first pivoting link and the second pivoting link to each other through screw fastening, a driven pulley member capable of fixing the first pivoting link to the pivot shaft through screw fastening, and a locking wire connected to the driver pulley member and the driven pulley member to transmit a rotational force from the driver pulley member to the driven pulley member. As the driver pulley member rotates, the driven pulley member rotates together, so that the fixing of the first pivoting link and the second pivoting link to each other and the fixing of the first pivoting link to the pivot shaft is accomplished simultaneously.

11 Claims, 7 Drawing Sheets

(51) Int. Cl.
*A61B 90/50* (2016.01)
*A61B 90/00* (2016.01)
*B25J 9/16* (2006.01)
*A61B 5/00* (2006.01)
*A61B 34/35* (2016.01)

(52) U.S. Cl.
CPC ............ *B25J 9/106* (2013.01); *B25J 9/1045* (2013.01); *B25J 9/1641* (2013.01); *A61B 5/0046* (2013.01); *A61B 34/35* (2016.02); *A61B 2034/715* (2016.02); *A61B 2090/506* (2016.02)

(56) References Cited

U.S. PATENT DOCUMENTS

| 9,669,542 | B2* | 6/2017 | Karguth | ................. B25J 9/1045 |
| 2003/0216821 | A1 | 11/2003 | Kim et al. | |
| 2010/0204578 | A1 | 8/2010 | Schmidt et al. | |
| 2017/0258539 | A1* | 9/2017 | Cohen | ................... A61B 34/70 |

FOREIGN PATENT DOCUMENTS

| JP | 3192459 U | 7/2014 |
| KR | 1020030022945 A | 3/2003 |
| KR | 20030088266 A | 11/2003 |

OTHER PUBLICATIONS

Rogier Barents et al., "Spring-to-Spring Balancing as Energy-Free Adjustment Method in Gravity Equilibrators," Journal of Mechanical Design, Jun. 2011, pp. 061010-1-061010-10, vol. 133.

Vigen Arakelian, "Gravity compensation in robotics," Advanced Robotics, 2016, pp. 79-96, vol. 30, No. 2.

* cited by examiner

GUIDING APPARATUS FOR REMOTE MEDICAL TREATMENTS

CROSS-REFERENCE TO RELATED APPLICATION

This application claims priority to Korean Patent Application No. 10-2017-0034578, filed on Mar. 20, 2017, and all the benefits accruing therefrom under 35 U.S.C. § 119, the contents of which in its entirety are herein incorporated by reference.

BACKGROUND

1. Field

The present disclosure relates to a guiding apparatus for remote medical treatments, and more particularly, to a guiding apparatus for remote medical treatments for guiding an end effector of an imaging module to assess the condition of a patient at a remote place.

[Description about National Research and Development Support]

This study was supported by Robot Industry Core Technology Development Project of Korea Evaluation Institute of Industrial Technology (Project Name: Development of remote existence robot system for supporting ICT-linked POC (Point of Care) service, Project No. 1415145626) under the superintendence of Ministry of Trade, Industry and Energy, Republic of Korea.

2. Description of the Related Art

A health care institution that is far from upper-class health care institution lacks sufficient number of medical staff, so there is a growing need to indirectly treat a patient at a remote place.

In remote treatments, for the upper-class health care institution to assess the condition of the patient, an imaging module including a camera is necessary for obtaining auditory and visual information of the patient. The patient condition information obtained through the imaging module can be transmitted to medical staff of the upper-class health care institution.

In this instance, to assess each body part of the patient more stably and efficiently, a guiding apparatus is necessary for easily guiding the position of the imaging module in treatments.

In addition to stable guiding, it is important that the guiding apparatus has a reliable operation structure not to cause unexpected damage to the patient. For example, an automatic manipulation type guiding apparatus has a risk of sudden movement in the control process.

On the other hand, a manual type guiding apparatus has high reliability because a user directly manipulates the guiding apparatus, but moving and fixing each link in the guiding apparatus is inconvenient, and in this process, the guiding apparatus itself may be contaminated, causing a secondary infection in the patient.

Therefore, a guiding apparatus for remote medical treatments that has a simple structure and can be manipulated more efficiently and stably is required.

SUMMARY

The present disclosure is directed to providing a guiding apparatus for remote medical treatments, in which not only links connected at a joint can be fixed by manipulation of a driver pulley member at the corresponding joint, but also links connected at another joint can be fixed.

To achieve the object, a guiding apparatus for remote medical treatments according to an embodiment of the present disclosure includes: a first pivoting link pivotally connected to a pivot shaft; a second pivoting link pivotally connected to the first pivoting link; a driver pulley member capable of fixing the first pivoting link and the second pivoting link to each other through screw fastening; a driven pulley member capable of fixing the first pivoting link to the pivot shaft through screw fastening; and a locking wire connected to the driver pulley member and the driven pulley member to transmit a rotational force from the driver pulley member to the driven pulley member, and as the driver pulley member rotates, the driven pulley member rotates together, so that the fixing of the first pivoting link and the second pivoting link to each other and the fixing of the first pivoting link to the pivot shaft is accomplished simultaneously.

According to an embodiment of the present disclosure, an end part of the driver pulley member may be screw-fastened to one of the first pivoting link and the second pivoting link, and the other pivoting link may be pivotally connected to the driver pulley member and may be fixed by screw fastening of the driver pulley member.

According to an embodiment of the present disclosure, the guiding apparatus for remote medical treatments may include a clamp fixed to the first pivoting link and surrounding the pivot shaft, and to which the driven pulley member is screw-fastened, and the clamp may be tightened by rotation of the driven pulley member to clamp the pivot shaft, so that the first pivoting link may be fixed to the pivot shaft.

According to an embodiment of the present disclosure, the guiding apparatus for remote medical treatments may include a tension adjustment member which is moveably connected to the first pivoting link, and placed in contact with the locking wire.

According to an embodiment of the present disclosure, the guiding apparatus for remote medical treatments may include: a gravity compensation link pivotally connected to the second pivoting link; and a gravity compensation spring connected to the gravity compensation link such that the gravity compensation spring is stretched or contracted as the gravity compensation link moves.

According to an embodiment of the present disclosure, the guiding apparatus for remote medical treatments may include a moveable pulley which is moveably connected to the gravity compensation link and to which the gravity compensation spring is fixed, and as the moveable pulley moves, the gravity compensation spring may be stretched or contracted.

According to an embodiment of the present disclosure, the guiding apparatus for remote medical treatments may include: a second driven pulley member capable of fixing the gravity compensation link and the second pivoting link to each other through screw fastening; and a second locking wire connected to the driver pulley member and the second driven pulley member to transmit a rotational force from the driver pulley member to the second driven pulley member, and as the driver pulley member rotates, a first driven pulley member may rotate and the first pivoting link may be fixed to the pivot shaft, and the second driven pulley member may rotate and the gravity compensation link may be fixed to the second pivoting link, so that the fixing of the first pivoting link and the second pivoting link to each other may be accomplished simultaneously.

According to an embodiment of the present disclosure, the guiding apparatus for remote medical treatments may include a camera connected to an end part of the gravity compensation link.

According to an embodiment of the present disclosure, the camera may be detachably connected to the gravity compensation link.

According to an embodiment of the present disclosure, the guiding apparatus for remote medical treatments may include a support to which the pivot shaft is fixed, the support being configured to be moveable.

According to an embodiment of the present disclosure, the first pivoting link may be detachably connected to the pivot shaft.

DETAILED DESCRIPTION

Hereinafter, a guiding apparatus for remote medical treatments according to an embodiment of the present disclosure is described with reference to the accompanying drawings.

Figure 1:
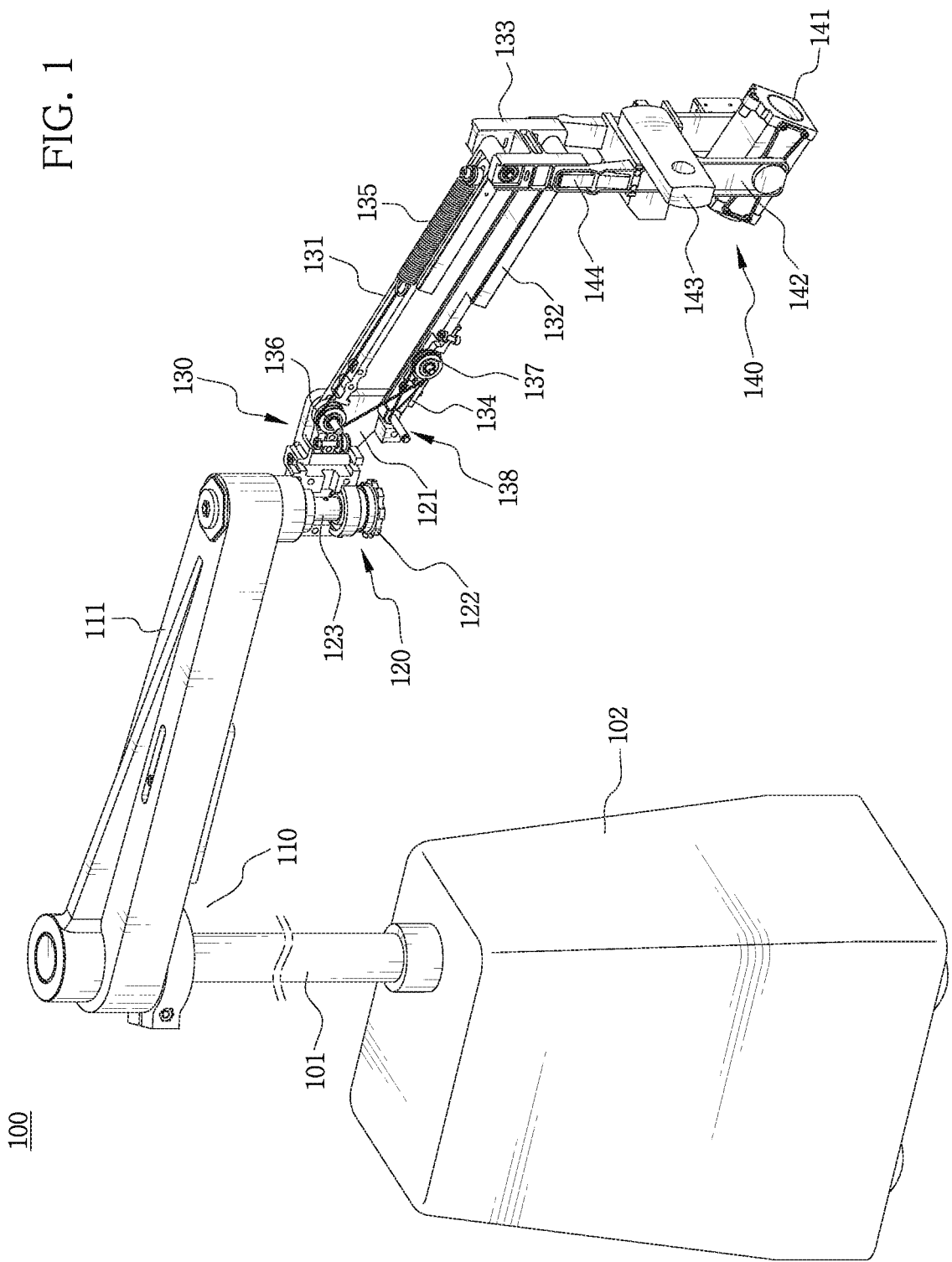
FIG. 1 is a partial cutaway perspective view of a guiding apparatus for remote medical treatments according to an embodiment of the present disclosure.
Figure 2:
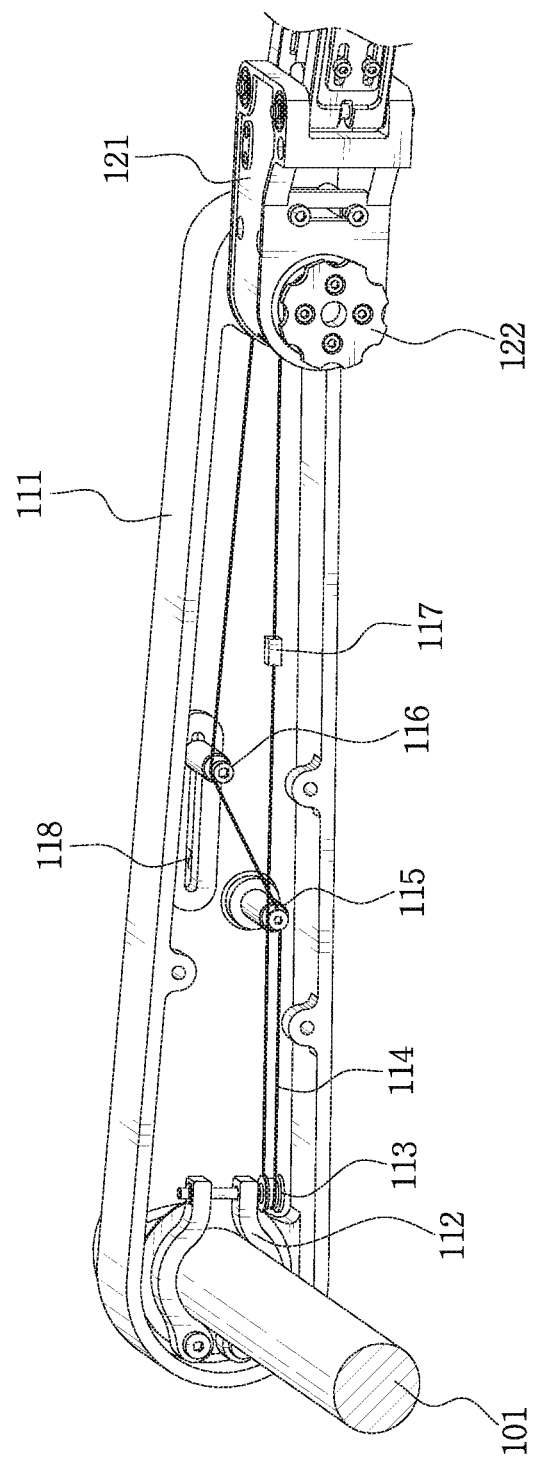
FIG. 2 is a partially enlarged cutaway perspective view of the guiding apparatus for remote medical treatments of FIG. 1 showing a first pivoting link.
Figure 3:
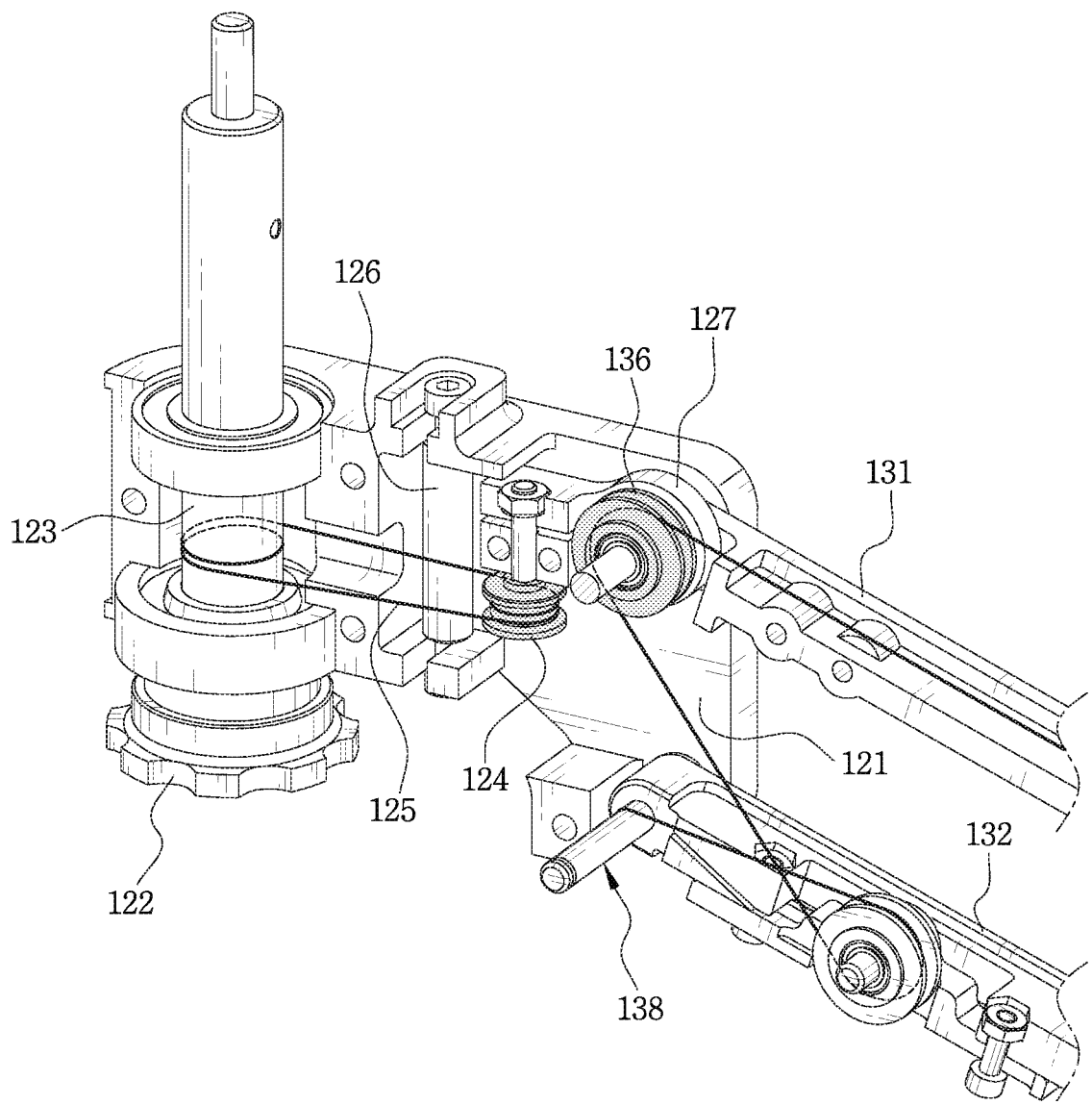
FIG. 3 is a partially enlarged cutaway perspective view of the guiding apparatus for remote medical treatments of FIG. 1 showing a second pivoting link.

Referring to FIGS. 1 to 3, a first pivoting link 111 is pivotally connected to a pivot shaft 101. The pivot shaft 101 may extend from a support 102 in the vertical direction. The pivot shaft 101 is preferably formed with sufficient height to allow persons to pass under the first pivoting link 111 connected to the top of the pivot shaft 101. Furthermore, the pivot shaft 101 may be extendable or contractable in the form of a telescopic tubes to enable height adjustment.

The pivot shaft 101 is fixed to the support 102. The support 102 may be configured to be moveable, for example, in the form of a mobile robot. Thereby, the guiding apparatus 100 can easily move to an optimal position to the body of a patient in use or before, thereby maximizing the convenience. On the other hand, the support 102 may be configured as a plate fixed to the bottom, not as shown.

On the other hand, the first pivoting link 111 is preferably formed with sufficient length for an end effector 140 as described below to reach the entire body of the patient that will be positioned at the side of the pivot shaft 101 as the first pivoting link 111 pivots around the pivot shaft 101.

A second pivoting link 121 is pivotally connected to the end part of the first pivoting link 111 on the opposite side to the pivot shaft 101. The second pivoting link 121 is shorter than the first pivoting link 111 and pivots in the horizontal direction, so that the horizontal direction position of the end effector 140 can be adjusted more precisely through manipulation of the second pivoting link 121. The pivoting direction and extended length of the second pivoting link 121 can be appropriately set according to specific uses.

The first pivoting link 111 and the second pivoting link 121 are connected to each other by a driver pulley member 123 at a second joint 120. The driver pulley member 123 is engaged with the first pivoting link 111 and the second pivoting link 121 simultaneously. The driver pulley member 123 may be screw-fastened with the first pivoting link 111 by threads formed at the end part, upwards through the second pivoting link 121. The second pivoting link 121 may be supported upwards by the driver pulley member 123 and pivotally connected to the driver pulley member 123.

On the other hand, although the first pivoting link 111 is shown as being placed above the second pivoting link 121, the second pivoting link 121 may be placed above the first pivoting link 111, and the driver pulley member 123 may be screw-fastened with the second pivoting link 121 through the first pivoting link 111.

When the driver pulley member 123 is fully engaged with the first pivoting link 111, the second pivoting link 121 is pressed from the top down and from the bottom up, respectively, by the lower surface of the first pivoting link 111 and the head part pressing surface of the driver pulley member 123, so that the second pivoting link 121 is fixed by the force of friction to keep it from pivoting relative to the first pivoting link 111.

When the driver pulley member 123 is partially released from the first pivoting link 111, the second pivoting link 121 can pivot relative to the first pivoting link 111. When the driver pulley member 123 is partially released, threads formed in the driver pulley member 123 and the first pivoting link 111 are preferably formed with moderate inclination and thread height long enough to prevent the driver pulley member 123 from continuously rotating in the draw direction by the pivoting of the second pivoting link 121, and to stably support the second pivoting link 121 upwards.

Power may be separately transmitted through a power means (not shown) to operate the driver pulley member 123, but the driver pulley member 123 is equipped with a locking handle 122 at the bottom and can be manually manipulated, and this is advantageous in terms of load reduction and manipulation easiness.

A first clamp 112 surrounding the pivot shaft 101 is fixed to the first pivoting link 111. The first clamp 112 may be open to the second joint 120. Two end parts on the open side of the first clamp 112 may be connected by a first driven pulley member 113. The first driven pulley member 113 passes through one of the two end parts of the first clamp 112 and is screw-fastened with the other end part, and can tighten or loosen the first clamp 112 according to the extent of engagement.

When the first driven pulley member 113 rotates in the engagement direction, the first clamp 112 is tightened and the force of friction between the first clamp 112 and the pivot shaft 101 increases, so that the first pivoting link 111 is fixed to keep it from pivoting around the pivot shaft 101.

On the contrary, when the first driven pulley member 113 is partially released, the first clamp 112 is loosened and the force of friction between the first clamp 112 and the pivot shaft 101 reduces, so that the first pivoting link 111 can pivot around the pivot shaft 101.

The driver pulley member 123 and the first driven pulley member 113 are connected by a first locking wire 114. The first locking wire 114 transmits the rotational force from the driver pulley member 123 to the first driven pulley member 113, allowing the first driven pulley member 113 to rotate simultaneously with the rotation of the driver pulley member 123.

When a user holds the locking handle 122 and rotates the driver pulley member 123 in the lock direction, the first locking wire 114 is wound on the driver pulley member 123 in one direction, and the first driven pulley member 113 rotates together by the tension of the first locking wire 114.

As the first driven pulley member 113 also rotates in the lock direction, when the first pivoting link 111 is fully engaged with the second pivoting link 121, the first clamp 112 also fully tightens the pivot shaft 101, so that the second pivoting link 121 can be fixed to the first pivoting link 111, and the first pivoting link 111 can be fixed to the pivot shaft 101.

When the driver pulley member 123 is released in the release direction, the first locking wire 114 is wound on the driver pulley member 123 in the opposite direction, and the first driven pulley member 113 rotates together in the opposite direction by the opposite direction tension of the first locking wire 114.

As the first driven pulley member 113 also rotates in the release direction, when the first pivoting link 111 is sufficiently released from the second pivoting link 121, the first clamp 112 is also sufficiently released from the pivot shaft 101, so that the second pivoting link 121 is released from the first pivoting link 111 and can pivot, and the first pivoting link 111 also can pivot around the pivot shaft 101.

The first locking wire 114 is preferably rigidly fixed to the driver pulley member 123 and the first driven pulley member 113, for example, in a manner of winding the first locking wire 114 on a through-hole formed in the pulley, to allow the driver pulley member 123 and the first driven pulley member 113 to transmit the rotational force to each other without running idle in each pulley groove.

The first locking wire 114 can maintain the tense condition by a wire guide member 115 and a first tension adjustment member 116. The first tension adjustment member 116 can slidably move on a tension adjustment groove 118, and by moving the first tension adjustment member 116 within the tension adjustment groove 118 according to the tension required to transmit the rotational force, the first locking wire 114 can be maintained in tense condition. The two ends of the first locking wire 114 are connected by a wire connecting member 117, so that the first locking wire 114 can surround the driver pulley member 123 and the first driven pulley member 113.

A first gravity compensation link 131 and a second gravity compensation link 132 may be connected to the distal end side of the second pivoting link 121. The end parts on the distal end side of each of the first gravity compensation link 131 and the second gravity compensation link 132 may be connected by a vertical link 133. The end effector 140 may be connected to the bottom of the vertical link 133.

On the other hand, it will be easily understood by those skilled in the art that connection of additional link or the end effector to the distal end side of the second pivoting link 121 includes the illustrated connection as well as various combinations.

The first gravity compensation link 131 is pivotally connected to the top of the second pivoting link 121. The second gravity compensation link 132 is pivotally connected to the bottom of the second pivoting link 121. At a third joint 130, the position where the second pivoting link 121 and the first gravity compensation link 131 are connected is placed immediately above the position where the second pivoting link 121 and the second gravity compensation link 132 are connected.

The first gravity compensation link 131 and the second gravity compensation link 132 extend with the same length. The vertical link 133 is connected to the distal end side of each gravity compensation link 131, 132. Although the gravity compensation links 131, 132 vertically pivot with respect to the second pivoting link 121, the vertical link 133 may be always placed such that its extension direction is perpendicular to the ground. That is, the first gravity compensation link 131, the second gravity compensation link 132, the second pivoting link 121, and the vertical link 133 are interconnected at four points, always forming a parallelogram.

On the other hand, locking of the gravity compensation links 131, 132 can be accomplished at the same time as locking of the first pivoting link 111 and the second pivoting link 121, and its detailed description is made below.

A second clamp 127 surrounding a pivot shaft around which the first gravity compensation link 131 pivots is fixed to the second pivoting link 121. The second clamp 127 may be open to the second joint 120.

Two end parts on the open side of the second clamp 127 may be connected by a second driven pulley member 124. The second driven pulley member 124 passes through one of the two end parts of the second clamp 127 and is screw-fastened with the other end part, and can tighten or loosen the second clamp 127 according to the extent of engagement.

When the second driven pulley member 124 rotates in the engagement direction, the second clamp 127 is tightened and the force of friction between the second clamp 127 and the pivot shaft increases, so that the first gravity compensation link 131 is fixed to keep it from pivoting around the pivot shaft.

On the contrary, when the second driven pulley member 124 is partially released, the second clamp 127 is loosened and the force of friction between the second clamp 127 and the pivot shaft reduces, so that the first gravity compensation link 131 can pivot around the pivot shaft.

The driver pulley member 123 and the second driven pulley member 124 are connected by a second locking wire 125. The second locking wire 125 transmits the rotational force from the driver pulley member 123 to the second driven pulley member 124, allowing the second driven pulley member 124 to rotate simultaneously with the rotation of the driver pulley member 123.

When a user holds the locking handle 122 and rotates the driver pulley member 123 in the lock direction, the second locking wire 125 is wound on the driver pulley member 123 in one direction, and the second driven pulley member 124 rotates together by the tension of the second locking wire 125.

As the second driven pulley member 124 also rotates in the lock direction, the second clamp 127 fully tightens the pivot shaft of the first gravity compensation link 131, so that the first gravity compensation link 131 can be fixed to the second pivoting link 121.

When the driver pulley member 123 is released in the release direction, the second locking wire 125 is wound on the driver pulley member 123 in the opposite direction, and the second driven pulley member 124 rotates together in the opposite direction by the opposite direction tension of the second locking wire 125.

As the second driven pulley member 124 also rotates in the release direction, the second clamp 127 is sufficiently released from the pivot shaft, so that the first gravity compensation link 131 is released from the pivot shaft and can pivot.

The second locking wire 125 is preferably rigidly fixed to the driver pulley member 123 and the second driven pulley member 124 to allow the driver pulley member 123 and the second driven pulley member 124 to transmit the rotational force to each other without running idle in each pulley groove.

The second locking wire 125 can maintain the tense condition by a second tension adjustment member 126. The second tension adjustment member 126 can slidably move on a tension adjustment groove, and by moving the second tension adjustment member 126 according to the extent required to transmit the rotational force, the second locking wire 125 can be maintained in tense condition.

The two ends of the second locking wire 125 are connected by a wire connecting member, so that the second locking wire 125 can surround the driver pulley member 123 and the second driven pulley member 124.

As described above, the rotational force of the driver pulley member 123 is transmitted to the driven pulley members 113, 124 by the locking wires 114, 125, so that the first pivoting link 111, the second pivoting link 121, and the first gravity compensation link 131 can be fixed at each joint 110, 120, 130 to keep them from pivoting.

It is important to design in consideration of the number of revolutions of the driver pulley member 123 and the driven pulley members 113, 124, so that the pivoting links 111, 121 are fixed by the driver pulley member 123, and at the same time, each clamp 112, 127 is contracted by the locking wires 114, 125, and thus the first pivoting link 111 is fixed to the pivot shaft 101, and the first gravity compensation link 131 and the second pivoting link 121 are fixed.

By accomplishing locking at each joint 110, 120, 130 via rotational force transmission by the locking wires 114, 125, faulty fixation caused by occurrence of an error can be lessened.

Furthermore, the use of a hand-operated structure has effects in ensuring reliability and stability of manipulation, reducing the tool load, and saving costs.

Figure 4:
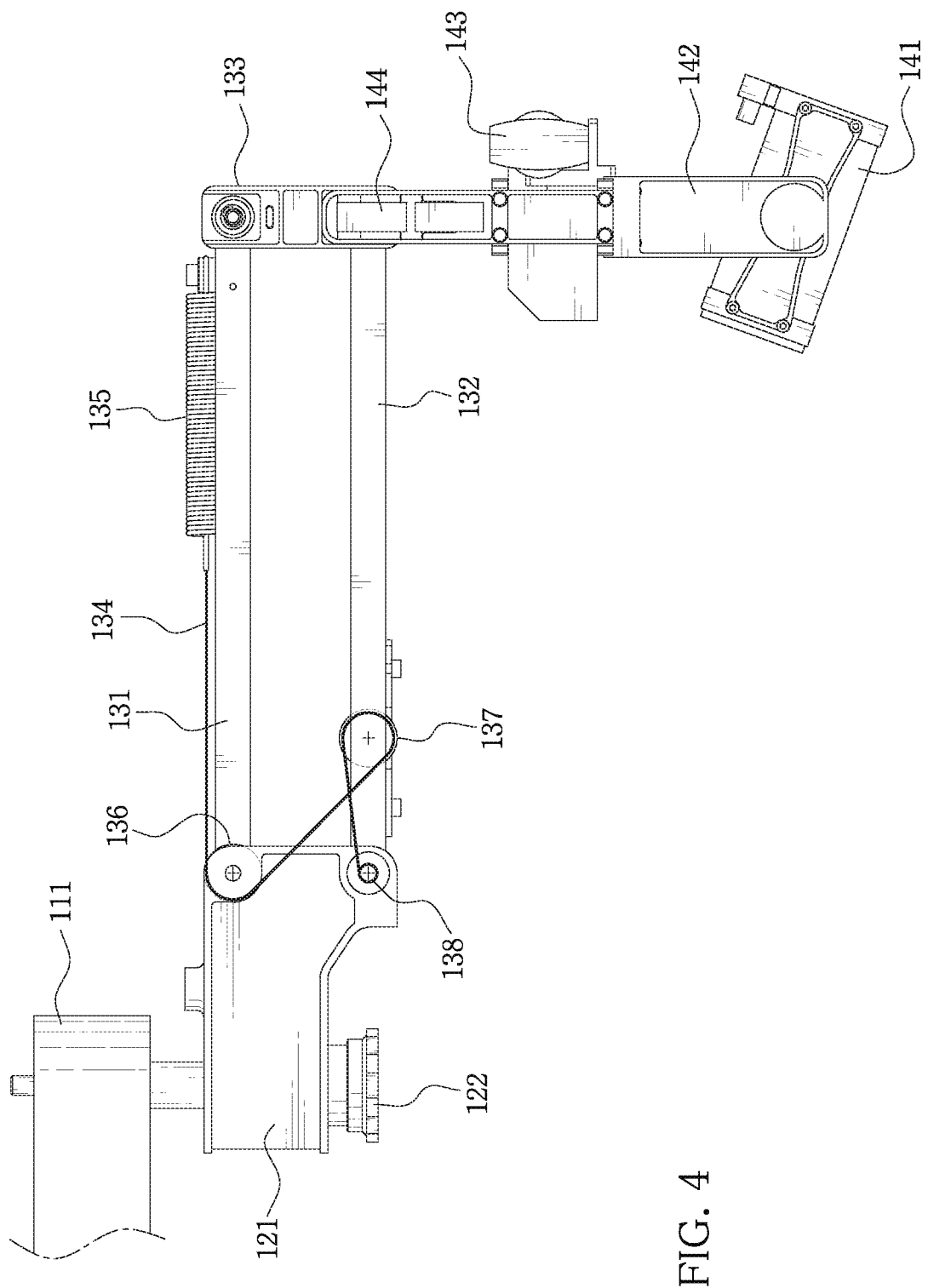
FIG. 4 is a partially enlarged side cross-sectional view of the guiding apparatus for remote medical treatments of FIG. 1 showing a gravity compensation link.

Referring to FIG. 4, the self-load of the gravity compensation links 131, 132, the vertical link 133, and the end effector 140 can be compensated for by the elastic force of a gravity compensation spring 135.

One end of the gravity compensation spring 135 may be fixed to the distal end side of the first gravity compensation link 131, and the other end may be fixed to the second gravity compensation link 132 by a gravity compensation wire 134.

The gravity compensation wire 134 is connected to a fixed pulley 136 provided at the third joint 130 and a moveable pulley 137 slide-moveably provided at the second gravity compensation link 132. The gravity compensation wire 134 may be fixed to a wire fixing part 138 provided on the proximal end side of the second gravity compensation link 132.

It is possible to design so that the elastic force is provided as much as the self-weight by extension or contraction of the gravity compensation spring 135, taking into account that as the gravity compensation links 131, 132 move up and down, the end portion including the end effector 140 changes in the center of gravity.

By compensating for the self-weight of the gravity compensation links 131, 132 and the end effector 140 using the gravity compensation spring 135 based on the spring constant K obtained, it is possible to fix the gravity compensation links 131, 132 at a desired position without directly grasping the gravity compensation links 131, 132, thereby ensuring easiness of manipulation.

On the other hand, by adjusting the extent of stretch of the gravity compensation spring 135 in initial condition with the movement of the moveable pulley 137, it is possible to enable gravity compensation even though the weight is different according to the type of the end effector 140.

Figure 5:
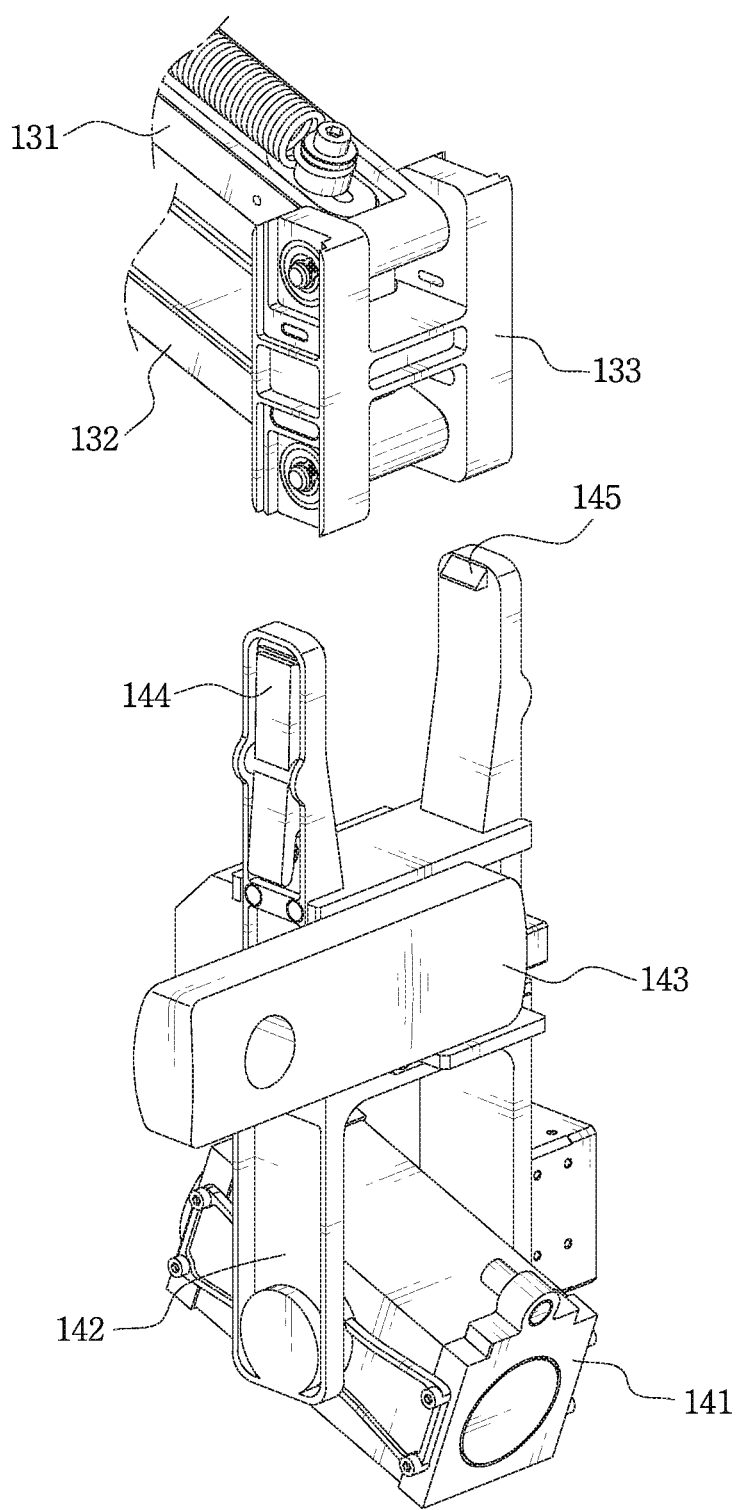
FIG. 5 is a partially enlarged exploded perspective view of the guiding apparatus for remote medical treatments of FIG. 1 showing an end effector.

Referring to FIG. 5, the end effector 140 may be mounted on the bottom of the vertical link 133. The end effector 140 may have a zoom camera 141 and a binocular 360 degree camera 143 rotatable connected to a fixed frame 142.

A release lever 144 having a protruding stopper member 145 may be provided at the top of the fixed frame 142. The end effector 140 can be attached to or detached from the vertical link 133 by inserting the stopper member 145 into grooves formed in the vertical link 133 or separating the stopper member 145 from the grooves by manipulation of the release lever 144. As the end effector 140 is formed into attachable and detachable structure, it is possible to hold the end effector 140 in hands for body imaging of the patient according to situations.

Figure 6:
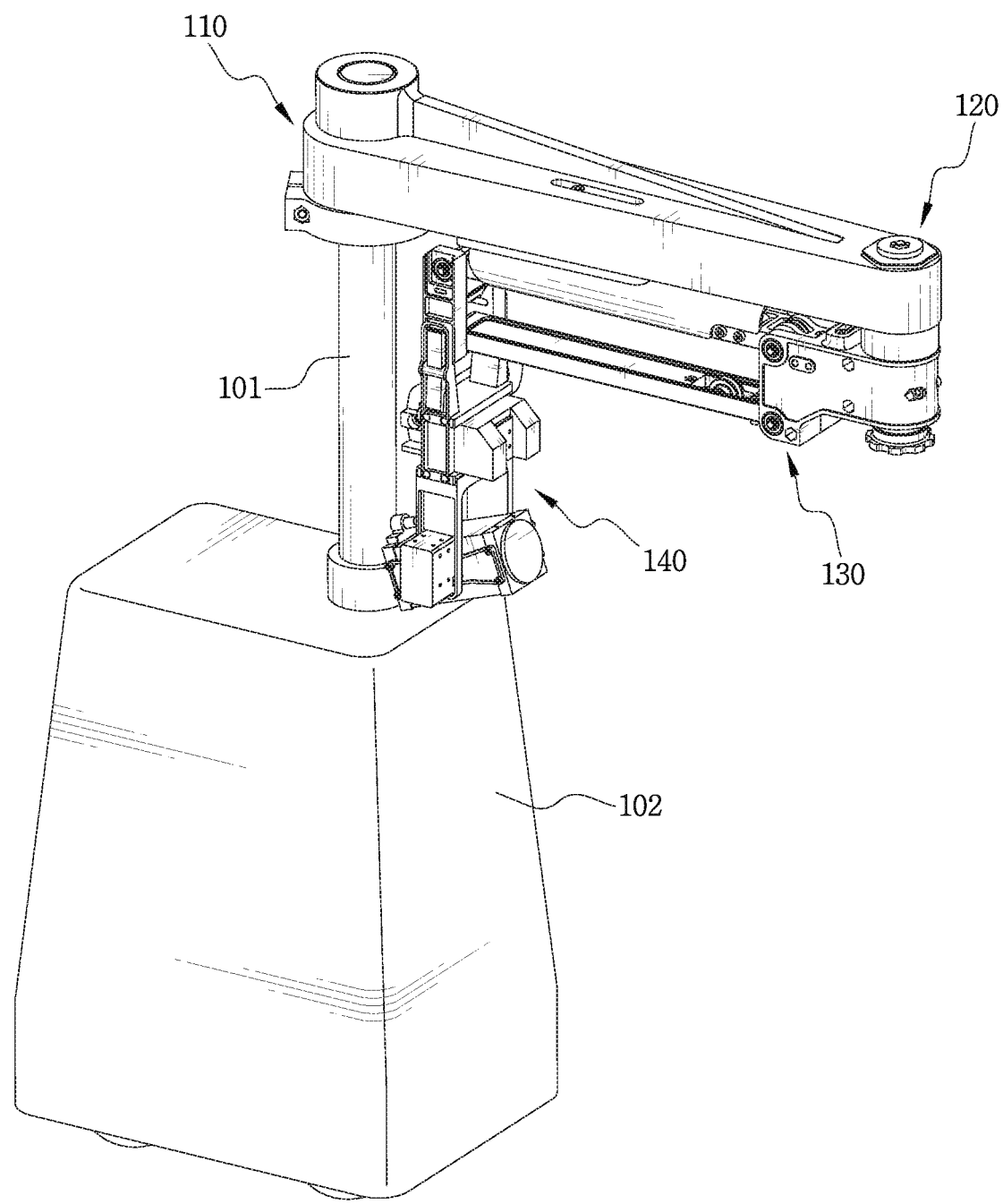
FIG. 6 is a perspective view of the guiding apparatus for remote medical treatments of FIG. 1 showing a retracted condition.

Referring to FIG. 6, the second pivoting link 121 and the first gravity compensation link 131 may be placed such that they overlap with the first pivoting link 111. The length of the first pivoting link 111 is greater than the sum of lengths of the second pivoting link 121 and the first gravity compensation link 131, and when the second joint 120 and the third joint 130 are placed closer to the pivot shaft 101 than the first joint 110, the second pivoting link 121 and the first gravity compensation link 131 may overlap with the first pivoting link 111.

Thereby, the space occupied by the guiding apparatus 100 when stored can be minimized. On the other hand, as the pivot shaft 101 is formed into extendable or contractable structure, the pivot shaft 101 can be contracted to the maximum extent when stored, in order to minimize the height of the space occupied by the guiding apparatus 100.

Figure 7:
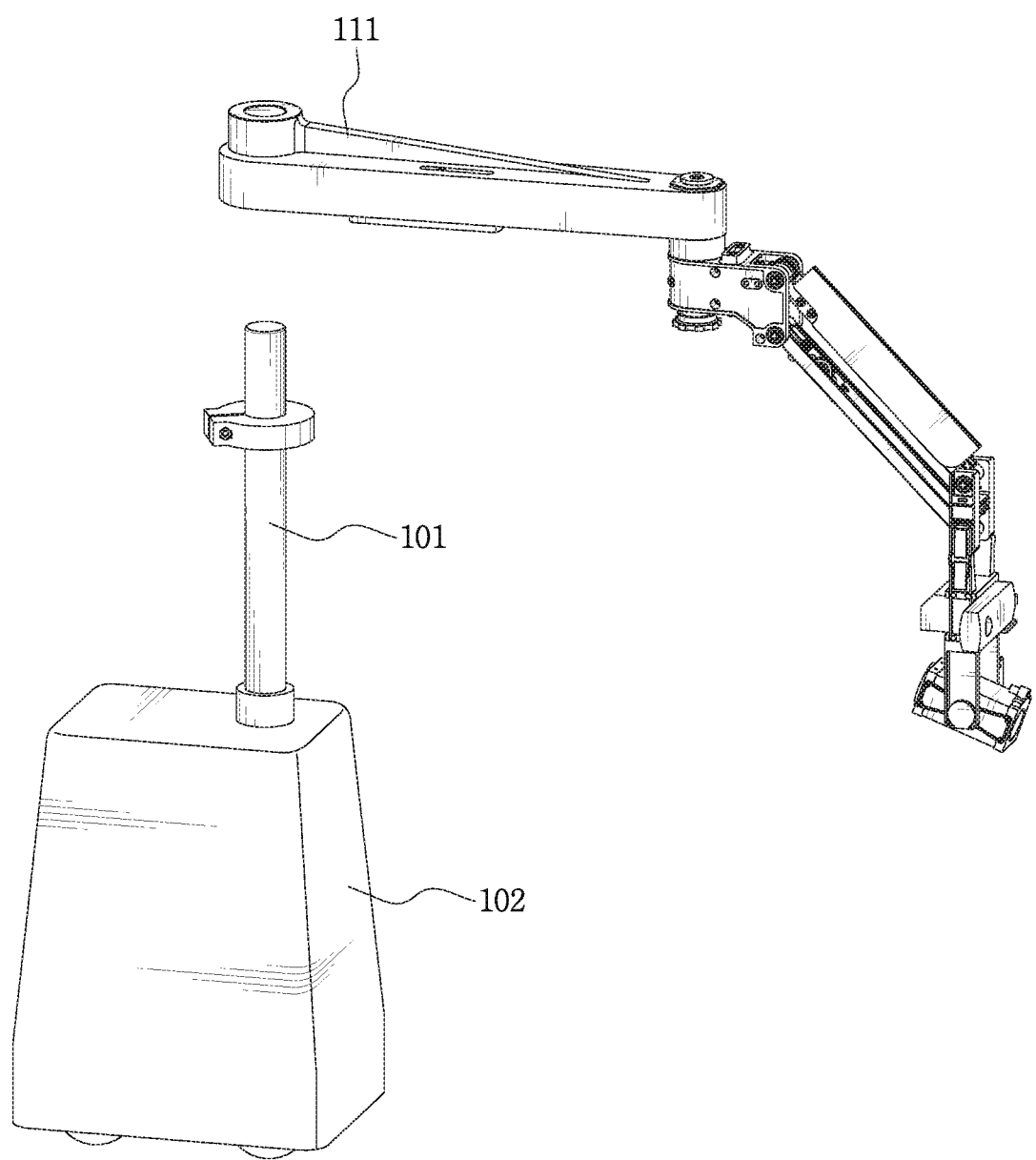
FIG. 7 is a perspective view of the guiding apparatus for remote medical treatments of FIG. 1 showing a separated condition.

Referring to FIG. 7, the first pivoting link 111 may be detachably connected to the pivot shaft 101. Thereby, the first pivoting link 111 is connected to the pivot shaft 101 when used, and the first pivoting link 111 is separated from the pivot shaft 101 when stored, hence the pivot shaft 101 and the support 102 section and the link section can be individually stored.

What is claimed is:

1. A guiding apparatus for remote medical treatments comprising:
    a first pivoting link pivotally connected to a pivot shaft;
    a second pivoting link pivotally connected to the first pivoting link;
    a driver pulley member capable of fixing the first pivoting link and the second pivoting link to each other through screw fastening;
    a driven pulley member capable of fixing the first pivoting link to the pivot shaft through a screw fastening structure thereof; and a locking wire connected to the driver pulley member and the driven pulley member to transmit a rotational force from the driver pulley member to the driven pulley member, wherein as the driver pulley member rotates, the driven pulley member rotates together, so that the fixing of the first pivoting link and the second pivoting link to each other and the fixing of the first pivoting link to the pivot shaft is accomplished simultaneously.

2. The guiding apparatus for remote medical treatments according to claim 1, wherein an end part of the driver pulley member is screw-fastened to one of the first pivoting link and the second pivoting link, and the other pivoting link is pivotally connected to the driver pulley member and is fixed by screw fastening of the driver pulley member.

3. The guiding apparatus for remote medical treatments according to claim 1, further comprising:

a clamp fixed to the first pivoting link and surrounding the pivot shaft, and to which the driven pulley member is screw-fastened, wherein the clamp is tightened by rotation of the driven pulley member to clamp the pivot shaft, so that the first pivoting link is fixed to the pivot shaft.

4. The guiding apparatus for remote medical treatments according to claim 1, further comprising:

a tension adjustment member slide-moveably connected to the first pivoting link, and placed in contact with the locking wire.

5. The guiding apparatus for remote medical treatments according to claim 1, further comprising:

a gravity compensation link pivotally connected to the second pivoting link; and a gravity compensation spring connected to the gravity compensation link such that the gravity compensation spring is stretched or contracted as the gravity compensation link moves.

6. The guiding apparatus for remote medical treatments according to claim 5, further comprising:

a moveable pulley slide-moveably connected to the gravity compensation link and to which the gravity compensation spring is fixed, wherein as the moveable pulley moves, the gravity compensation spring is stretched or contracted.

7. The guiding apparatus for remote medical treatments according to claim 5, further comprising:

a second driven pulley member capable of fixing the gravity compensation link and the second pivoting link to each other through screw fastening; and a second locking wire connected to the driver pulley member and the second driven pulley member to transmit a rotational force from the driver pulley member to the second driven pulley member, wherein as the driver pulley member rotates, a first driven pulley member rotates and the first pivoting link is fixed to the pivot shaft, and the second driven pulley member rotates and the gravity compensation link is fixed to the second pivoting link, so that the fixing of the first pivoting link and the second pivoting link to each other is accomplished simultaneously.

8. The guiding apparatus for remote medical treatments according to claim 5, further comprising:

a camera connected to an end part of the gravity compensation link.

9. The guiding apparatus for remote medical treatments according to claim 8, wherein the camera is detachably connected to the gravity compensation link.

10. The guiding apparatus for remote medical treatments according to claim 1, further comprising:

a support to which the pivot shaft is fixed, the support being configured to be moveable.

11. The guiding apparatus for remote medical treatments according to claim 1, wherein the first pivoting link is detachably connected to the pivot shaft.

* * * * *